United States Patent
Subramanian et al.

(10) Patent No.: US 9,167,831 B2
(45) Date of Patent: Oct. 27, 2015

(54) SOLID, EDIBLE, CHEWABLE LAXATIVE COMPOSITION

(71) Applicant: Gavis Pharmaceuticals, LLC, Somerset, NJ (US)

(72) Inventors: Veerappan Sellappan Subramanian, Mendham, NJ (US); Paranjothy Kanni, Mendham, NJ (US)

(73) Assignee: Gavis Pharmaceuticals, LLC, Somerset, NJ (US)

( * ) Notice: Subject to any disclaimer, the term of this patent is extended or adjusted under 35 U.S.C. 154(b) by 0 days.

(21) Appl. No.: 13/856,731

(22) Filed: Apr. 4, 2013

(65) Prior Publication Data

US 2013/0267608 A1    Oct. 10, 2013

Related U.S. Application Data

(60) Provisional application No. 61/620,724, filed on Apr. 5, 2012.

(51) Int. Cl.
| | |
|---|---|
| *A61K 9/00* | (2006.01) |
| *A23G 3/36* | (2006.01) |
| *A61K 9/06* | (2006.01) |
| *A61K 47/36* | (2006.01) |
| *A61K 31/765* | (2006.01) |

(52) U.S. Cl.
CPC ............. *A23G 3/36* (2013.01); *A61K 9/0056* (2013.01); *A61K 9/0087* (2013.01); *A61K 9/06* (2013.01); *A61K 31/765* (2013.01); *A61K 47/36* (2013.01)

(58) Field of Classification Search
CPC ...................................... A61K 31/765
USPC .......................................... 514/723
See application file for complete search history.

(56) References Cited

U.S. PATENT DOCUMENTS

| | | | | |
|---|---|---|---|---|
| 5,928,664 | A * | 7/1999 | Yang et al. ............. | 424/440 |
| 8,337,915 | B2 * | 12/2012 | Aburdeineh et al. ......... | 424/757 |
| 2004/0115282 | A1 * | 6/2004 | Keiser et al. .................. | 424/601 |
| 2013/0295018 | A1 * | 11/2013 | Motoyama et al. ........... | 424/9.4 |

OTHER PUBLICATIONS

Nesba et al. (2007).*
Bastin, Sandra, "The Science of Jam and Jelly Making", University of Kentucky, College of Agriculture, UK Cooperative Extension Service, Bulletin FN-SSB.110, (1995), 2 pgs.

* cited by examiner

*Primary Examiner* — Zohreh Fay
(74) *Attorney, Agent, or Firm* — Schwegman Lundberg & Woessner, P.A.

(57) ABSTRACT

An edible, solid composition comprising a laxative and one or more bulking agents in aqueous media wherein the laxative is polyethylene glycol and the composition is prepared by dissolving the polyethylene glycol in aqueous media together with one or more bulking agents and subjecting the mixture to heat up to at least about 100° C.

14 Claims, No Drawings

SOLID, EDIBLE, CHEWABLE LAXATIVE COMPOSITION

CLAIM OF PRIORITY

This application claims the benefit of priority of U.S. Provisional Application Ser. No. 61/620,724, filed on Apr. 5, 2012, which application is herein incorporated by reference in its entirety.

BACKGROUND

Polyethylene glycol (PEG), particularly PEG 3350 is a known osmotic laxative. PEG 3350 is sold in US in laxative compositions which typically are to be combined with an aqueous medium. For example 17 g of PEG powder is dissolved in about 8 ounces of aqueous beverage and consumed to provide a laxative dosage. Examples of such products include Miralax® (MSD consumer care) and Gavilax® (Gavis Pharmaceuticals, NJ).

Formulation of PEG as a beverage or in an aqueous medium is inconvenient, unsatisfying and uncomfortable to the consumer. The aqueous formulation has an undesirable mouth-feel and can create a bloated, overwhelmed feeling in the consumer's stomach. The aqueous formulation is also not a drink that can be discretely consumed so that consumers typically use restrooms in which to mix and drink the formulation. This practice is uncomfortable, disagreeable and ill tasting. The discomfort and inconvenience leads to reduction of dose compliance of the product as directed. Thus, there is a need for more conveniently dosed polyethylene glycol.

While there are certain products, for example Movicol® (Norgine Ltd, Middx UB9 6NS, UK) that are sachets for combination with aqueous media, they contain in addition to polyethylene glycol, electrolytes such as sodium chloride, sodium bicarbonate and potassium chloride. These salts do not impart good taste and suffer from the same discomfort and inconvenience as an aqueous formulation containing only PEG.

Other laxatives formulated for oral consumption suffer from the same problems. All have disagreeable tastes, cause a bloated feeling in the stomach and require inconvenient mixing as aqueous formulations. Chief among these are the laxative preparations with water insoluble substances such as psyllium, bran husk, microcrystalline cellulose and the like. These all form gritty distasteful aqueous formulations that leave thick residue in the glass when drunk.

Therefore, there is a need to provide a laxative dosage form that has a good taste and would enhance patient compliance.

SUMMARY OF INVENTION

The present invention is directed to a laxative based edible, solid composition. An aspect of the invention provides that the composition preferably is formed as a gummy bear. According to another aspect of the invention, the composition of such ingredients as a laxative, a bulking agent and an optional sweetening agent are included.

A further aspect of the invention provides that the solid composition is formed as an edible gummy bear by heating the ingredients to form a fluid dispersion in water and cooling the fluid dispersion, preferably in a mold to form a solid composition. In particular, and preferably, another aspect of the invention provides that the laxative is first melted or otherwise converted into a flowable viscous to fluid state in water with heating. The additional ingredients are then combined with the fluid and mixed to form the hot fluid dispersion. An aspect of invention is a sweetening agent, preferably sugar and a polymer such as pectin, preferably added together to the fluid dispersion. Another preferred aspect of invention is an organic acid such as Citric acid and a polyol such as maltilol are added after addition of Pectin and sugar. The fluid dispersion is added to molds preferably sized to produce mouth-sized pieces, and allowed to cool to ambient temperature.

According to yet another aspect of the invention, the dispersion constituting the chewable, edible composition is solid at ambient temperature.

Additional aspects of the invention provide that the composition may optionally include electrolytes such as sodium chloride, sodium bicarbonate and potassium chloride. Other optional aspects include sweeteners and flavoring agents that can also be added to the composition as appropriate. Specialized flavors that target saltiness can be also advantageously utilized to reduce the salty taste according to further aspects of the invention.

DETAILED DESCRIPTION

The objective was to develop a gummy bear formulation that will have an elastic rubbery texture with a good mouth feel and taste. Several bulking agents such as Gelatin, Modified starches and Pectin were tried. Pectin was found to work better in gelling with PEG 3350. With Starch and Gelatin, PEG 3350 was separating and in some cases producing a harder unacceptable or in some cases a sticky product. Pectin in combination with Corn syrup or Maltilol, and sugar produced a good jelly gummy bear with PEG 3350. PEG mw's range from 400 to 40,000, preferably 600 to 10,000, most preferably 1000 to 6000.

Maltitol was found to be better than Corn syrup with respect to addition and mixing. Order of addition, controlling the Brix parameters and in-process controls were found to be important in manufacturing good quality Gummy bears.

A preferred order of addition in purified water was found as follows:
1. Polyethylene glycol such as PEG 3350
2. Sweetening agent preferably Sugar
3. Polymer preferably pectin
4. Organic acid preferably citric acid
5. Polyol such as Maltitol Preferably Sugar and Pectin are added together as a mixture.

Brix Assessment: Brix is used in the food industry to measure the Total Soluble Solids (TSS) in the product. It has been found that brix value between 70° Brix to 80° Brix, preferably between 75° to 78° gave satisfactory product. This brix was generally been able to achieve between temperature 100° C. and 115° C., more preferably 108° C. to 110° C. It is also preferred to have constant mixing throughout the process to prevent any inhomogeneity of the product. RB-115-084 was chosen as the proto-type formula and a mini-pilot batch (RBMP-115-089) was taken with a batch size of 1600 gms (70 gummy bears).

TABLE 1

Gummy Bears (gms)

| Item | Ingredients | RB115-039 | RB115-040 | RB115-041 | RB115-043 | RB115-044 | RB115-045 |
|---|---|---|---|---|---|---|---|
| 1 | Purified Water | 36.000 | 2.888 | 2.888 | 2.888 | 3.99 | 4.000 |
| 2 | PEG 3350 | — | 4.000 | 4.000 | 4.000 | 4.000 | 4.000 |
| 3 | Pectin | 4.000 | 0.320 | 0.320 | 0.240 | 0.328 | 0.240 |
| 4 | Sugar | 41.000 | 3.280 | 3.280 | 3.280 | 4.52 | 3.280 |
| 5 | Citric acid | 1.600 | 0.128 | 0128 | 0.128 | 0.182 | 0.128 |
| 6 | Corn Syrup | 50.000 | 4.000 | 4.000 | 4.000 | 5,44 | 4.000 |
| 7 | Strawberry Flavor | 0.125 | 0.010 | 0.020 | 0.020 | 0.020 | 0.020 |
|  | Total Wt | 132.725 | 14.618 | 14.628 |  |  |  |
|  | Comments | Placebo Base Expt Soft gummy bears Good taste | Tastes good Hard gummies | Tastes good Hard gummies | Tastes good Texture not good Hard gummies | Tastes good Texture not good | Tastes good Soft but sticky |
|  | Procedure | 39: Keep water under stirring and heating Mix Sugar and pectin together and add to the bulk. Add Citric acid and mix. Add Corn syrup and mix. Continue heating to 120° C. Cool to 90° C. Add the flavor. Pour in to mold. Cool to set. 040: Same as 039. PEG 3350 is added and mixed well. 041, 043 & 044: Same as 040 with increased quantity of flavor. 045: Keep water under stirring and heating. Mix Pectin and Sugar together and add to the bulk. Add PEG3350 and dissolve. Add Corn syrup and mix. Add Citric acid and mix. Monitor heating and mixing to 120° C. Start cooling. When the temperature falls down to 100° C. add the flavor and mix well. Pour into molds and cool to set. | | | | | |

TABLE 2

Gummy Bears

| Item # | Ingredients | RB-115-046 | RB-115-047 | RB-115-048 | RB-115-049 | RB-115-050 | RB-115-051 |
|---|---|---|---|---|---|---|---|
| 1 | Purified Water | 3.00 | 3.00 | 3.000 | 3.000 | 3.000 | 3.000 |
| 2 | PEG 3350 | 2.000 | 1.000 | — | 1.000 | 2.000 | 3.000 |
| 3 | Pectin | 0.320 | 0.320 | 0.320 | 0.320 | 0.320 | 0.320 |
| 4 | Sugar | 3.280 | 3.280 | 3.280 | 3.280 | 3.280 | 3.280 |
| 5 | Citric acid | — | — | 0.128 | 0.128 | 0.128 | 0.128 |
| 6 | Corn Syrup | 4.000 | 4.000 | 4.000 | 4.000 | 4.000 | 4.000 |
| 7 | Red # 40 | 0.0002 | 0.0002 | 0.0002 | 0.0002 | 0.0002 | 0.0002 |
| 8 | Strawberry Flavor |  |  | 0.040 | 0.040 | 0.040 | 0.040 |
|  | Total Wt |  |  |  |  |  |  |
|  | Comments | Taste good Sticky Unrecoverable from mold | Tate good Sticky Unrecoverable From mold | With out PEG Tastes good Releases from mold easily | Good taste Releases from mold easily | Sticky Does not release from mold | Sticky Does not release from mold |
|  | Procedure | 046: Keep water under stirring and heating. Mix Pectin and Sugar together and add to the bulk. Add PEG 3350 and mix. Add Corn Syrup and mix. Continue heating and mixing to 115° C. Stop heating and start cooling. When the temperature falls down to 100° C. add color and mix well. Pour into molds and cool to set (Citric acid is necessary to form a jelly). 047: Same as 046 048: Same as 047. Placebo batch. PEG not added (Citric acid is important) 049: Dissolve PEG3350 in water in a container and keep under stirring. Mix Sugar and pectin together and add to the bulk. Add citric acid and mix. Add Corn Syrup and mix. Start heating and monitor heating to 115° C. Stop heating and start cooling. When the temperature falls down to 100° C. add color and flavor, mix well. Pour in to molds and cool to set. 050: Same as 049 051: Same as 049 | | | | | |

TABLE 3

Gummy Bears

| # | Ingredients | RB-115-052 | RB-115-054 | R8-115-055 | RB-115-057 | RB-115-058 | RB-115-059 |
|---|---|---|---|---|---|---|---|
| 1 | Purified Water | 3.000 | 3.000 | 3.000 | 3.200 | 3.000 | 3.000 |
| 2 | PEG 3350 | 4.000 | 1.000 | 1.600 | 2.00 | 1.400 | 1.400 |
| 3 | Pectin | 0.320 | 0.320 | 0.600 | 0.600 | 0.600 | 0.600 |
| 4 | Sugar | 3.280 | 3.280 | 3.600 | 3.600 | 3.600 | 3.600 |
| 5 | Citric acid | 0.128 | 0.128 | 0.140 | 0.140 | 0.140 | 0.140 |
| 6 | Corn Syrup | 4.000 | 4.000 | 4.000 | 4.000 | — | — |
| 7 | Maltitol Syrup | — | — | — | — | 4.000 | 4.000 |
| 8 | Red # 40 | 0.0002 | 0.0002 | 0.0002 | 0.0002 | 0.002 | — |
| 9 | Strawberry Flavor | 0.040 | 0.040 | 0.048 | 0.048 | 0.048 | — |
| 10 | D&C yellow | | | | | | 0.0002 |
| 11 | Lemon flavor | | | | | | 0.048 |
| | Total Wt | | | | | | |
| | Comments | Not good | 49 - reproduced Slightly Sticky | Good product | Not good | Maltitol Can Replace Corn Syrup | Good product Good taste |
| | Procedure | 052: Same as 049 | | | | | |
| | | 054: Same as 049 | | | | | |
| | | 055: Same as 049. Pectin quantity is increased | | | | | |
| | | 057: Same as 049. PEG quantity is increased | | | | | |
| | | 058: Same as 049. Corn Syrup is replaced with Maltitol Syrup. | | | | | |
| | | 059: Same as 049. Color is DC yellow and Flavor is Lemon. | | | | | |

TABLE 4

Gummy Bears

| # | Ingredients | RB-115-060 Each Gummy bear of 20 gm contains | RB-115-061 | RB-115-066 | RB-115-076 | RB-115-077 | RB-115-078 | RB-115-84 |
|---|---|---|---|---|---|---|---|---|
| 1 | Purified Water | 5.357 | 5.357 | 5.357 | 5.357 | 5.357 | 5.357 | 5.357 |
| 2 | PEG 3350 | 2.500 | 2.500 | 2.500 | 2.500 | 2.500 | 2.500 | 2.500 |
| 3 | Pectin | 1.071 | 1.071 | 1.071 | 1.071 | 1.071 | 1.071 | 1.071 |
| 4 | Sugar | 6.429 | 6.429 | 6.429 | 6.429 | 6.429 | 6.429 | 6.429 |
| 5 | Citric acid | 0.250 | 0.250 | 0.250 | 0.250 | 0.250 | 0.250 | 0.250 |
| 6 | Maltitol Syrup | 7.142 | 7.142 | 7.142 | 7.142 | 7.142 | 7.142 | 7.142 |
| 7 | Red # 40 | 0.00035 | 0.00035 | — | — | — | — | — |
| 8 | Orance shade color | — | — | — | 0.0005 | 0.0005 | 0.0005 | 0.0005 |
| 9 | Strawberry Flavor | — | — | — | — | — | — | — |
| 10 | Mixed berry flavor | 0.0857 | 0.0857 | — | — | — | — | — |
| 11 | Orange Flavor | | | 0.0857 | 0.0857 | 0.107 | 0.0857 | 0.0857 |
| | Comments | Texture not good. Needs process improvement Brix could not rise beyond 62° | Good taste Good Texture Brix 76.9° at 110° | Good Taste Good Texture | Adding pectin & Sugar at 50° C. causes problem | Good taste Good texture Brix 76.5° at 110° C. | Good taste Good texture Brix 76° at 110° C. | Good taste Good texture Brix 76.5° at 110° C. |
| | Procedure | 060: Dissolve PEG 3350 in Purified water in a container and keep under stirring. Mix Sugar and pectin together and add to the solution under stirring. Add the citric acid. Add Maltitol syrup and mix for 10 minutes. Add the color and mix well. Start heating and continue to monitor till it reaches 110° C. Add Flavor and mix well. Check the brix and weight of the pulp before pouring to the molds. Pour into silicon molds (20 gms) and cool to set. | | | | | | |
| | | 061: Repetition of 059. With mixed berry flavor | | | | | | |
| | | 066: Same as 059 with orange flavor | | | | | | |
| | | 076: Same as 059 with orange color and flavor | | | | | | |
| | | 077: Dissolve PEG3350 in water under stirring to form a clear solution. Mix Pectin and Sugar together add to the bulk and mix well. Add Maltitol syrup and mix well for 10 minutes. | | | | | | |

TABLE 4-continued

Gummy Bears

| # | Ingredients | RB-115-060 Each Gummy bear of 20 gm contains | RB-115-061 | RB-115-066 | RB-115-076 | RB-115-077 | RB-115-078 | RB-115-84 |
|---|---|---|---|---|---|---|---|---|

Start heating and monitor till 110° C. Check the brix. Add the flavor and color and mix well.
Pour the hot mixture in to molds and cool to set. The gummies are carefully removed,
dusted with corn starch and packed
078: Same as 077 with monitoring of brix periodically.
084: repetition of 078

TABLE 5

Gummy bears with PEG and Electrolytes

| Item | Ingredients | RB-115-085 (14 × 20 gms) | RB-115-085 Per Each | |
|---|---|---|---|---|
| 1 | P. Water | 75.000 | 5.360 | gms |
| 2 | PEG 3350 | 35.000 | 2.500 | gms |
| 3 | Sod.Chloride | 0.924 | 0.066 | gms |
| 4 | Pot.Chloride | 0.126 | 0.009 | gms |
| 5 | Sod.bicarb | 0.476 | 0.034 | gms |
| 6 | Pectin | 15.000 | 1.070 | gms |
| 7 | Sugar | 90.000 | 6.420 | gms |
| 8 | Citric acid | 3.500 | 0.250 | gms |
| 9 | Maltitol Syrup | 100.000 | 7.140 | gms |
| 10 | Orange color | 0.007 | 0.500 | mg |
| 11 | Orange Flavor | 1.260 | 0.090 | gms |
| | Total wt | 321.293 | 22.949 gms | |
| | Comments | End point is 280 gms Each gummy bear weighs about 20 gms Each gummy bear contains 2.5 gms of PEG 3350 | End point is 20 gms Each gummy bear weighs about 20 gms Each gummy bear contains 0.066 gms of Sod. Chloride 0.009 gms of Pot. Chloride 0.034 gms of Pot. bicarb | 2.5 gms of PEG 3350 0.066 gms of Sod. Chloride 0.009 gms of Pot. Chloride 0.034 gms of Pot. bicarb |

Procedure

Dissolve PEG 3350 in Purified water in a container and keep under stirring. Add the salts one by one and dissolve. Mix Sugar and pectin together and add to the solution under stirring. Add the citric acid. Add Maltitol syrup and mix for 10 minutes. Add the color and mix well. Start heating and continue to monitor till it reaches 110° C. Add the flavor and mix well. Check the brix and weight of the pulp before pouring to the molds. Pour into silicon molds (20 gms) and cool to set.

TABLE 6

Gummy bears with PEG alone

| Item # | Ingredients | RB-115 084 (14 × 20 gm) | RB-115 084 Per Each | RBMP-115-089 |
|---|---|---|---|---|
| 1 | P. Water | 75.000 | 5.360 gms | 5.360 |
| 2 | PEG 3350 | 35.000 | 2.500 gms | 2.500 |
| 3 | Pectin | 15.000 | 1.070 gms | 1.071 |
| 4 | Sugar | 90.000 | 6.420 gms | 6.428 |
| 5 | Citric acid | 3.500 | 0.250 gms | 0.250 |
| 6 | Maltitol Syrup | 100.000 | 7.140 gms | 7.142 |
| 7 | Orange color | 0.007 | 0.500 mg | 0.001 |
| 8 | Orange Flavor | 1.200 | 0.090 gms | 0.093 |
| | Total wt | 319.707 | 22.830 gms | 22.843 |
| | Comments | End weight is 280 gms Each gummy bear weighs about 20 gms Each gummy bear will contain about 2.5 gms of PEG 3350 | End weight is 20 gms Each gummy bear weighs about 20 gms Each gummy bear will contain about 2.5 gms of PEG 3350 | Taste Texture - Good End weight is 20 gms Each gummy bear weighs about 20 gms Each gummy bear will contain about 2.5 gms of PEG 3350 |

Procedure

Dissolve PEG 3350 in Purified water in a container and keep under stirring. Mix Sugar and pectin together and add to the solution under stirring. Add the citric acid. Add Maltitol syrup and mix for 10 minutes. Add the color and mix well. Start heating and continue to monitor till it reaches 110° C. Add the flavor and mix well. Check the brix and weight of the pulp before pouring to the molds. Pour into silicon molds (20 gms) and cool to set.

The invention claimed is:

1. An edible, solid composition consisting essentially of a cooked laxative product of polyethylene glycol, pectin, sugar, citric acid, water, one or both of corn syrup and maltitol syrup, an optional flavor ingredient, and an optional electrolyte ingredient, wherein the polyethylene glycol has a molecular weight of from 600 to 10,000, wherein the weight ratio of pectin to polyethylene glycol to a combination of sugar, and one or both of corn syrup and maltitol syrup is about 1 to about 2-3 to about 12-13, the cooked product at a temperature of at least 100° C. has a Brix value of 70° to 80°, at ambient temperature, the cooked product has a texture and consistency like that of a gummy bear formulation and the cooked product is free of gelatin, starch and modified starch.

2. The edible, solid composition according to claim 1 wherein the cooked product contains maltitol not corn syrup.

3. The edible, solid composition according to claim 1 wherein the cooked product contains at least 8 weight percent polyethylene glycol relative to the total weight of the cooked product.

4. The edible, solid composition according to claim 1 wherein the molecular weight of the polyethylene glycol is about 1000 to 6000.

5. The edible, solid composition according to claim 4 wherein the molecular weight of the polyethylene glycol is about 3350.

6. The edible, solid composition according to claim 1 wherein the concentration of polyethylene glycol is from about 8 wt % to about 13 wt % relative to the total weight of the cooked product.

7. The edible, solid composition according to claim 1 wherein the cooked product has a weight ratio for pectin to polyethylene glycol to the combination, of about 1 to 2.3-2.7 to 12.6-12.8.

8. The edible solid composition according to claim 1 having a total weight of about 20 grams.

9. The edible solid composition according to claim 1 wherein the composition is one or more pieces of a gummy bear formulation, each weighing about 20 grams.

10. An intermediate formulation suitable for forming a gummy bear laxative composition of claim 1, the formulation consisting essentially of water, polyethylene glycol, pectin, citric acid, sugar, one or both of corn syrup and maltitol syrup optional flavor and electrolyte ingredients wherein the formulation has a Brix value of about 70° to about 80° at a temperature of at least about 100° C., the weight percent of polyethylene glycol is at least 8 wt percent relative to the total weight of the formulation, the weight ratio of pectin to polyethylene glycol to a combination of sugar and one or both of corn syrup or maltitol syrup is about 1 to about 2-3 to about 12-13 and the formulation is free of gelatin, starch and modified starch.

11. A process for producing a gummy bear laxative comprising:
    forming a mixture of at least water, polyethylene glycol, pectin, citric acid, a bulking agent of polyol, corn syrup, sugar or any combination thereof, and optional flavor and electrolyte ingredients, wherein the polyethylene glycol has a molecular weight of from 600 to 10,000, and is present at least at 8 weight percent relative to the total weight of the composition;
    heating the mixture to a temperature of at least about 100° C. until the Brix of the mixture is about 70° to about 80° to form a cooked mixture; and
    cooling the cooked mixture to produce the gummy bear laxative as a cooked gel.

12. A process according to claim 11 wherein the weight ratio of pectin to polyethylene glycol to bulking agent is about 1 to about 2-3 to about 12-20.

13. A gummy bear laxative prepared by the process of claim 11.

14. The edible solid composition according to claim 1 wherein the cooked product contains corn syrup not maltitol syrup.

* * * * *